US009247735B2

(12) United States Patent
Bristow

(10) Patent No.: US 9,247,735 B2
(45) Date of Patent: Feb. 2, 2016

(54) CROP PLANT-COMPATIBLE HERBICIDAL COMPOSITIONS CONTAINING HERBICIDES AND SAFENERS

(75) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 216 days.

(21) Appl. No.: 13/009,031

(22) Filed: Jan. 19, 2011

(65) Prior Publication Data
US 2012/0184435 A1    Jul. 19, 2012

(51) Int. Cl.
*A01N 25/32* (2006.01)
*A01N 47/36* (2006.01)
*A01N 57/14* (2006.01)

(52) U.S. Cl.
CPC ............... *A01N 25/32* (2013.01); *A01N 47/36* (2013.01); *A01N 57/14* (2013.01)

(58) Field of Classification Search
CPC ....... A01N 47/36; A01N 43/40; A01N 57/14; A01N 2300/00; A01N 25/32
USPC ........................................................ 504/103
See application file for complete search history.

(56) References Cited

U.S. PATENT DOCUMENTS

| H0000806 H | * | 8/1990 | Keifer et al. | 504/108 |
| 5,516,750 A | * | 5/1996 | Willms et al. | 504/106 |
| 6,855,667 B2 | * | 2/2005 | Keifer | 504/103 |
| 2005/0009702 A1 | | 1/2005 | Keifer | |

FOREIGN PATENT DOCUMENTS

| EP | 0 509 433 A1 | 10/1992 |
| EP | 0 520 371 A2 | 12/1992 |
| WO | WO 91/18907 | 12/1991 |
| WO | WO 92/03053 | 3/1992 |

OTHER PUBLICATIONS
Office Action dated Feb. 13, 2013, in corresponding French Patent Application No. 1250394.
International Search Report and Written Opinion dated Feb. 16, 2012, in corresponding PCT Application No. PCT/CN2011/081898.

* cited by examiner

*Primary Examiner* — Janet Epps-Smith
*Assistant Examiner* — Courtney Brown
(74) *Attorney, Agent, or Firm* — Dickinson Wright PLLC

(57) ABSTRACT

Disclosed herein are herbicidal compositions, characterized in that they comprise:
A) an antidotically effective amount of one or more safeners from the group of the phosphorated esters of the formula (I):

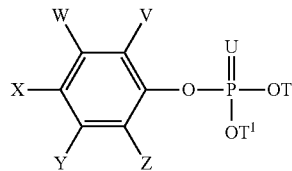

wherein
T and $T^1$ are independently selected from the group of hydrogen, alkyl, haloalkyl, alkoxyalkyl, alkenyl, and alkynyl;
U is O or S, and
V, W, X, Y, and Z are independently selected from the group of hydrogen, halogen, alkyl, haloalkyl, and alkoxy; and
B) one or more sulfonamide or sulfonylurea herbicides selected from the group consisting of amidosulfuron, azimsulfuro bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, thifensulfuron-methyl, tribenuron-methyl, trifloxysulfuron, triflusulfuron-methyl, triosulfuron, cloransulammethyl, diclosulam, florasulam, flumetsulam, metosulam, penoxsulam, and combinations thereof, and methods for using the same.

24 Claims, No Drawings

CROP PLANT-COMPATIBLE HERBICIDAL COMPOSITIONS CONTAINING HERBICIDES AND SAFENERS

BACKGROUND

1. Field

Disclosed herein are crop protection compositions which can be used against unwanted vegetation and which contain, as active compounds, a combination of at least one herbicide and at least one safener.

2. Description of Related Art

Herbicides are useful for controlling unwanted vegetation, i.e. weeds, which may otherwise cause significant damage to desirable plant species such as crop plants or ornamentals. Many potent herbicides have the ability to control for full growing seasons and at low rates of application, a broad spectrum of grass and broadleaf weeds that compete with desirable plants or crops such as wheat, cotton, or corn. Unfortunately, certain potent herbicides are not tolerated by, or are phytotoxic to, a wide of desirable plants when applied at rates effective to control unwanted vegetation. For example, a large number of sulfonamide or sulfonylurea herbicides cannot thus be employed in maize, rice or cereals with sufficient selectivity. Phytotoxic side-effects become apparent on the crop plants in particular when these herbicides are applied post-emergence, and it is desirable to avoid or reduce such a phytotoxicity.

One approach to increasing the tolerance of sensitive crops to certain herbicides while maintaining broad spectrum weed control is through the use of genetically-modified crop seed lines that have tolerance to the otherwise phytotoxic herbicide. Unfortunately, high technology costs, as well as the discomfort of many consumers to the introduction of such genetically modified crops to the market, has rendered this solution of increasing the tolerance of crops to be inadequate.

It is already known to use certain herbicides in combination with certain compounds, known as "safeners" or "antidotes," which reduce the phytoxicity of the herbicides in crop plants without correspondingly reducing the herbicidal activity against the harmful plants. Such components in combination are termed "safened."

For example, the use of 5-phenylisoxazoline- and 5-phenylisothiazoline-3-carboxyl derivatives as safeners for herbicides from the series of the carbamates, thiocarbamates, haloacetanilides, phenoxyphenoxyalkanecarboxylic acid derivatives, sulfonylureas and the like has been mentioned in EP-A-509433.

EP-A-520371 mentions, inter alia, 5-alkylisoxazoline- and -isothiazoline-3-carboxyl derivatives as safeners for a range of classes of herbicides.

WO92/03053 mentions the use of substituted 3-arylisoxazoine- and -isothiazoline-5-carboxyl derivatives as safeners for certain herbicides. WO 91/18907 describes silyl-substituted isoxazolines, isoxazoles, isothiazolines and isothiazoles as crop protecting agents.

U.S. Pat. No. 5,516,750 mentions that compounds from the group of 5,5-disubstituted isoxazolines are outstandingly suitable for protecting crop plants against the damaging effects of aggressive agrochemicals, in particular herbicides.

However, in practice, the use of the herbicidal compositions mentioned in these publications is frequently associated with one or more disadvantages. For example, the herbicidal activity of the known compounds is not always sufficient, or, if the herbicidal activity is sufficient, then undesired damage to the useful plants can be observed.

U.S. Pat. No. 6,855,667 mentions the use of certain aromatic phosphate esters and thioesters as safeners for the herbicide clomazone. While other herbicides are mentioned in the disclosure, the only herbicide specifically exemplified is clomazone, and the only test results were on corn and cotton seeds; no results are provided for post-emergence application. Moreover, the only test results provided were for a single safener, dietholate, and the largest percent reduction in injury obtained was only 80.0%. This latter value was obtained by applying the safening compound to seeds as a seed treatment, and then later applying clomazone. The average reduction in injury reported in the patent was only 33.35% for cotton seed treatment and only 36.8% for both types of corn seed tested.

In view of the above, there remains a need in the art to provide herbicidal compositions having better properties than those described above.

SUMMARY

It has now been found that combinations of certain herbicides with a number of safeners are highly compatible with crops of useful plants and, at the same time, highly effective against unwanted harmful plants.

These advantages, as well as others, are provided by certain embodiments of selected herbicidal compositions, characterized in that they comprise:

A) an antidotically effective amount of one or more safeners from the group of the phosphorated esters of the formula (I):

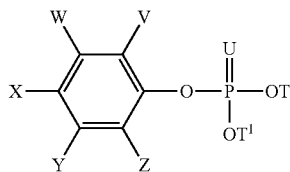

wherein

T and $T^1$ are independently selected from the group of hydrogen, alkyl, haloalkyl, alkoxyalkyl, alkenyl, and alkynyl;

U is O or S, and

V, W, X, Y, and Z are independently selected from the group of hydrogen, halogen, alkyl, haloalkyl, and alkoxy; and B) one or more sulfonamide or sulfonylurea herbicides selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, thifensulfuron-methyl, tribenuron-methyl, trifloxysulfuron, triflusulfuron-methyl, triosulfuron, cloransulam-methyl, diclosulam, florasulam, flumetsulam, metosulam, penoxsulam, and combinations thereof.

In particular, the herbicides rimsulfuron, thifensulfuron-methyl, nicosulfuron, tribenuron-methyl, metsulfuron-methyl, and combinations thereof are particularly suitable for use as component B.

Desirably, these compositions comprise component A and B in a weight ratio of A to B ranging from 1:10 to 10:1, in particular from 1:10 to 5:1.

Also desirably, compounds wherein T and $T^1$ are individually alkyl having 1-10 carbon atoms, more particularly, alkyl having 1-7 carbon atoms, even more particularly, alkyl having 1-4 carbon atoms are suitable for use as component A. Particularly suitable are compounds wherein T and $T^1$ are individually methyl, ethyl, propyl, or butyl, U is sulfur, and V, W, X, Y, and Z are each hydrogen.

Also disclosed herein is a method of protecting a plant from unintentional phytotoxic injury from application of a herbicidally-effective amount of a herbicidal compound to the locus of the plant, which method comprises applying to said locus an effective amount of one or more safening compounds phosphorated esters of the formula (I). In a particular embodiment, the method comprises applying to the locus of the plant the composition described above, wherein the herbicide and safener are applied simultaneously.

DETAILED DESCRIPTION OF SPECIFIC EMBODIMENTS

The embodiments disclosed herein generally relate to the field of crop protection compositions which can be used against unwanted vegetation and which comprise, as active compounds, a combination of at least one herbicide and at least one safener selected from phosphorated esters of the formula (I):

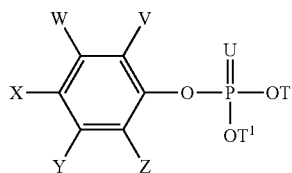

wherein
T and $T^1$ are independently selected from the group of hydrogen, alkyl, haloalkyl, alkoxyalkyl, alkenyl, and alkylnyl;
U is O or S, and
V, W, X, Y, and Z are independently selected from the group of hydrogen, halogen, alkyl, haloalkyl, and alkoxy.

As used herein the terms "about" and "approximately," when used in connection with a numerical value or range of values, denote the recited numerical value, as well as numerical amounts slightly higher than the numerical value and slightly lower than the numerical value (unless the numerical value represents a quantity of substance and the numerical value is zero); where one skilled in the art could not determine the meaning of the terms, they encompass a variation of, at most, ±10% of the numerical value.

As used herein and unless otherwise indicated, the substituent terms alkyl, alkenyl, alkynyl, alkoxy, and haloalkyl, used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. "Halogen" or "halo" refers to fluorine, bromine, iodine, or chlorine.

As set forth herein, there are many herbicides with varying degrees of selectivity and phototoxicity to both weeds and crops alike that could provide added utility if they were safened to a broader range of crops. The herbicidal compound or compounds include sulfonylureas and/or sulfonamides selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, thifensulfuron-methyl, tribenuron-methyl, trifloxysulfuron, triflusulfuron-methyl, triosulfuron, cloransulam-methyl, diclosulam, florasulam, flumetsulam, metosulam, penoxsulam, and combinations of these. In particular, combinations of rimsulfuron and thifensulfuron-methyl, thifensulfuron-methyl and tribenuron-methyl, rimsulfuron and nicosulfuron, and thifensulfuron-methyl and metsulfuron-methyl are particularly suitable.

Plants of interest that can be safened as described herein preferably include, without limitation, soybean, cotton, sugarbeet, rape, potato, sunflower, peanut, lettuce, carrot, sweet potato, alfalfa, tobacco, corn, rice, sorghum, wheat, barley, oats, rye, triticale, and sugarcane. More preferred plants on which to apply the compounds or the compositions of the present invention are soybean, wheat, corn, cotton, sugarbeet, rape, potato, sunflower, peanut, lettuce, carrot, sweet potato, alfalfa, and tobacco. The most preferred plants to which methods and compositions described herein are applied are wheat, corn, and cotton, especially corn and cotton.

The herbicidal active substances and the safener mentioned can be applied together (in the form of a ready-mix or by the tank mix method) or one after the other in any desired sequence. The ratio by weight of safener to herbicide can vary within wide limits and is preferably in a range of 1:10 to 10:1, in particular in a range of 1:10 to 5:1. The precise amounts of herbicide and safener which are used in each case will depend on the type of the herbicide used and/or on the safener used, as well on the nature of the plant to be treated, and can be determined in each individual case by using the information provided herein, as well as routine experimentation and suitable preliminary trials. Analogous ratios can be considered when safener and other active substances of crops protection products, such as insecticides or insecticide/herbicide combinations, are used.

The safeners are desirably mainly employed in cereal crops (wheat, rye, barley, oats), rice, maize, sorghum, but also in cotton and corn.

A particular advantage of the safener of the formula (I) described herein is to be found when they are combined with herbicides selected from the group consisting of the sulfonylureas and/or sulfonamides. Some herbicides of these structural classes cannot be employed, e.g., in cotton and corn, or cannot be employed with sufficient selectivity, without the safeners and techniques described herein. Outstanding and surprising selectivities can be achieved even with these difficult-to-employ herbicides in cotton and corn when the herbicides are combined with a safener according to the compositions and/or methods described herein.

Depending on their properties, the safener of the formula (I) can be used for pre-treating the seed of the crop plant, or they can be incorporated into the seed furrows prior to sowing, or applied together with the herbicidal before or after emergence of the plants. Pre-emergence treatment includes both the treatment of the area under cultivation before sowing and treatment of the area under cultivation where seed has been sown, but growth of the crop plants has not yet taken place. The joint use together with the herbicide, in particular by post-emergence methods, is preferred. Tank mixes or ready-mixes can be employed for this purpose. Any of these application methods are within the meaning of the term "applying to the locus of the plant," as that term is used herein.

Depending on the symptoms of crop damage and the herbicide used, the application rates of safener required can vary within wide limits and are, as a rule, in the range of 0.001 to 15 kg, preferably 0.005 to 5 kg, of active substance per hectare. In addition to the sulfonylurea and sulfonamide herbicides described herein, the compositions may contain additional pesticidal materials, including additional herbicides, such as fluoroxypyr. In particular, the combination of thifensulfuron-methyl and fluoroxypyr is particularly suitable.

Also disclosed herein are embodiments of a method of protecting crop plants against phytotoxic side-effects of pesticides, preferably herbicides, which comprises applying an effective amount of a compound of the formula (I) to the locus of the plants (e.g., to the plants, seeds of the plants, or the area under cultivation) before, after, or simultaneously with the pesticide or herbicide.

Also disclosed herein are crop-protecting products which comprise an active substance of the formula (I) and customary formulation auxiliaries, as well as to pesticidal, preferably herbicidal, compositions which comprise an active substance of the formula (I), and a pesticide or herbicide and formulation auxiliaries which are customarilly used in the field of crop protection.

The compounds of the formula (I) and/or their combinations with one or more of the herbicides mentioned can be formulated in a variety of ways, as determined by various biological and/or chemical-physical parameters. The following possibilities are therefore among those suitable for formulation: wettable powders (WP), emulsifiable concentrates (EC), water soluble powders (SP), water-soluble concentrates (SL), concentrated emulsions (EW), such as oil-in-water and water-in-oil emulsions, sprayable solutions or emulsions, capsules suspensions (CS), oil- or water-based dispersions (SC), suspoemulsions, dusts (DP), seed-dressing products, granules (GR) in the form of microgranules, spray granules, coated granules and adsorption granules, water-soluble granules (SG), water-dispersible granules (WG), ULV formulations, microcapsules and waxes.

Wettable powders are preparations which are uniformly dispersible in water and which, besides the active substance, also contain wetting agents, for example polyoxethylated alkylphenols, polyoxethylated fatty alcohols and fatty amines, fatty alcohol polyglycol ether sulfates, alkanesulfonates or alkylarylsulfonates, and dispersing agents, for example sodium lignosulfonate, sodium 2,2'-dinaphthylmethane-6,6'-disulfonate, sodium dibutylnaphthalenesulfonate or else sodium oleoylmethyltaurate, in addition to a diluent or inert substance.

Emulsifiable concentrates are prepared by dissolving the active substance in an organic solvent, for example butanol, cyclohexanone, dimethylformamide, xylene or else higher-boiling aromatics or hydrocarbons, with addition of one or more emulsifiers. Examples of emulsifiers which can be used include: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide ethylene oxide condensation products (for example block copolymers), alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite and pyrophyllite, or diatomaceous earth.

Granules can be prepared either by spraying a liquid containing the active substance onto adsorptive, granulated inert material or by applying active substance concentrates onto the surface of carriers, such as sand, kaolin or granulated inert material, by means of binders, for example polyvinyl alcohol, sodium polyacrylate or else mineral oils. Suitable active substances can also be granulated in the manner which is conventional for the production of fertilizer granules, if desired in the form of a mixture with fertilizers.

In general, the agrochemical preparations typically contain approximately 0.1 to 99 percent by weight, in particular approximately 0.1 to 95% by weight, of active substances of the formula (I) (antidote) or of the active substance mixture of antidote/herbicide, and approximately 1 to 99.9% by weight, in particular approximately 5 to 99.8% by weight, of a solid or liquid additive, and approximately 0 to 25% by weight, in particular approximately 0.1 to 25% by weight, of a surfactant.

The concentration of active substance in wettable powders is, for example, approximately 10 to 90% by weight, the remainder to 100% being composed of customary formulation components. In the case of emulsifiable concentrates, the concentration of active substance is approximately 1 to 80% by weight of active substances. Formulations in the form of dusts contain approximately 1 to 20% by weight of active substances, sprayable solutions approximately 0.2 to 20% by weight of active substances. In the case of granules, such as water-dispersible granules, the active substance content depends partly on whether the active compound is in liquid or solid form. In general, the water-dispersible granules typically contain between 10 and 90% by weight of active substance.

Besides, the active substances, the formulations mentioned contain, if appropriate, the adhesives, wetting agents, dispersants, emulsifiers, penetrants, solvents, fillers or carriers which are conventional in each case.

In use, the formulations, when provided in commercially available form, are, if appropriate, diluted in the customary manner, for example using water in the case of wettable powders, emulsifiable concentrates, dispersions and water-dispersible granules. Preparations in the form of dusts, granules and sprayable solutions are conventionally not diluted any further with other inert substances before they are used. The application rate of the antidotes required varies with the external conditions such as inter alia, temperature, humidity, and the nature of the pesticide or herbicide used.

EXAMPLES

In the examples below the term "technical" means the herbicidal compound as it is obtained from the manufacturing process, and typically includes 90-100 wt % of the active ingredient, with the remainder being inert additives, impurities, etc. All percentages are by weight, based upon the total weight of the composition.

Example 1

22.4% Rimsulfuron+Thifensulfuron methyl WG

| EXAMPLE 1: 22.4% Rimsulfuron + Thifensulfuron methyl WG (with safener) | | COMPARISON A: 22.4% Rimsulfuron + Thifensulfuron methyl WG (without safener) | | |
| --- | --- | --- | --- | --- |
| Component | Composition | Component | Composition | Remark |
| Rimsulfuron (technical) | 18.4% | Rimsulfuron (technical) | 18.4% | Active ingredient |

-continued

| EXAMPLE 1: 22.4% Rimsulfuron + Thifensulfuron methyl WG (with safener) | | COMPARISON A: 22.4% Rimsulfuron + Thifensulfuron methyl WG (without safener) | | |
|---|---|---|---|---|
| Component | Composition | Component | Composition | Remark |
| Thifensulfuron (techical) | 4% | Thifensulfuron (technical) | 4% | Active ingredient |
| O,O-dimethyl-O-phenyl phosphorothioate | 2.3% | O,O-dimethyl-O-phenyl phosphorothioate | 0 | safener |
| Sodium dodecylphenylsulfonate | 12% | Sodium dodecylphenylsulfonate | 12% | Dispersing agent |
| Naphthalene sulphonate, sodium salt | 3% | Naphthalene sulphonate, sodium salt | 3% | Wetting agent |
| Mannitol | Balance to 100% | Mannitol | Balance to 100% | filler |

The water-dispersible granules are obtained by mixing the above components according to the recipe, and grinding the mixture in a pine-disc mill to form a powder, and then granulating the powder in a fluidized bed by spraying on water as granulation liquid.

Example 2

54.5% Nicosulfuron WG

| EXAMPLE 2: 54.5% Nicosulfuron WG (with safener) | | COMPARISON B: 54.5% Nicosulfuron WG (without safener) | | |
|---|---|---|---|---|
| Component | Composition | Component | Composition | Remark |
| Nicosulfuron (technical) | 54.5% | Nicosulfuron (technical) | 54.5% | Active ingredient |
| O,O-dimethyl-O-phenyl phosphorothioate | 13.6% | O,O-dimethyl-O-phenyl phosphorothioate | 0 | safener |
| Sodium dodecylphenylsulfonate | 10% | Sodium dodecylphenylsulfonate | 10% | Dispersing agent |
| Naphthalene sulphonate, sodium salt | 2.6% | Naphthalene sulphonate, sodium salt | 2.6% | Wetting agent |
| Mannitol | Balance to 100% | Mannitol | Balance to 100% | filler |

The water-dispersible granules are obtained by mixing the above components according to the recipe, and grinding the mixture in a pine-disc mill to form a powder, and then granulating the powder in a fluidized bed by spraying on water as granulation liquid.

Example 3

75% Thifensulfuron-methyl+Tribenuron-methyl WG

| EXAMPLE 3: 75% Thifensulfuron-methyl + Tribenuron-methyl WG (with safener) | | COMPARISON C: 75% Thifensulfuron-methyl + Tribenuron-methyl WG (without safener) | | |
|---|---|---|---|---|
| Component | Composition | Component | Composition | Remark |
| Thifensulfuron-methyl (technical) | 50% | Thifensulfuron-methyl (technical) | 50% | Active ingredient |
| Tribenuron-methyl (technical) | 25% | Tribenuron-methyl (technical) | 25% | Active ingredient |
| O,O-dimethyl-O-phenyl phosphorothioate | 10% | O,O-dimethyl-O-phenyl phosphorothioate | 0 | safener |

-continued

| EXAMPLE 3: 75% Thifensulfuron-methyl + Tribenuron-methyl WG (with safener) | | COMPARISON C: 75% Thifensulfuron-methyl + Tribenuron-methyl WG (without safener) | | |
|---|---|---|---|---|
| Component | Composition | Component | Composition | Remark |
| Sodium dodecylphenylsulfonate | 5% | Sodium dodecylphenylsulfonate | 5% | Dispersing agent |
| Naphthalene sulphonate, sodium salt | 2.6% | Naphthalene sulphonate, sodium salt | 2.6% | Wetting agent |
| Mannitol | Balance to 100% | Mannitol | Balance to 100% | filler |

The water-dispersible granules are obtained by mixing the above components according to the recipe, and grinding the mixture in a pine-disc mill to form a powder, and then granulating the powder in a fluidized bed by spraying on water as granulation liquid.

Example 4

40 g/L Nicosulfuron OD

| EXAMPLE 4: 40 g/L Nicosulfuron OD (with safener) | | COMPARISON D: 40 g/L Nicosulfuron OD (without safener) | | |
|---|---|---|---|---|
| Component | Composition | Component | Composition | Remark |
| Nicosulfuron (technical) | 50% | Nicosulfuron (technical) | 50% | Active ingredient |
| O,O-diethyl-O-phenyl phosphorothioate | 10% | O,O-diethyl-O-phenyl phosphorothioate | 0 | safener |
| Sodium dodecylphenylsulfonate | 5% | Sodium dodecylphenylsulfonate | 5% | Dispersing agent |
| Nonyl phenoxy polyethyleneoxy ethanol | 5% | Nonyl phenoxy polyethyleneoxy ethanol | 5% | Co-dispersing agent |
| Magnesium Aluminium Silicate | 0.5% | Magnesium Aluminium Silicate | 0.5% | Thickening agent |
| Vegetable oil | Balance to 100% | Vegetable oil | Balance to 100% | diluent |

The oil-base suspension concentrate are obtained by mixing all the above components according to the recipe, and milling the mixture using a horizontal agitating bead mill maintaining appropriate process parameters, such as the average particle size, as is conventional in this field.

Example 5

20% Rimsulfuron+Nicosulfuron SG

| EXAMPLE 5: 22.4% Rimsulfuron + Nicosulfuron SG (with safener) | | COMPARISON E: 22.4% Rimsulfuron + Nicosulfuron SG (without safener) | | |
|---|---|---|---|---|
| Component | Composition | Component | Composition | Remark |
| Rimsulfuron (technical) | 10% | Rimsulfuron (technical) | 10% | Active ingredient |
| Nicosulfuron (technical) | 10% | Nicosulfuron (technical) | 10% | Active ingredient |
| O,O-diethyl-O-phenyl phosphorothioate | 20% | O,O-diethyl-O-phenyl phosphorothioate | 0 | safener |

-continued

| EXAMPLE 5: 22.4% Rimsulfuron + Nicosulfuron SG (with safener) | | COMPARISON E: 22.4% Rimsulfuron + Nicosulfuron SG(without safener) | | |
|---|---|---|---|---|
| Component | Composition | Component | Composition | Remark |
| Sodium dodecylphenylsulfonate | 12% | Sodium dodecylphenylsulfonate | 12% | Dispersing agent |
| Naphthalene sulphonate, sodium salt | 3% | Naphthalene sulphonate, sodium salt | 3% | Wetting agent |
| Mannitol | Balance to 100% | Mannitol | Balance to 100% | filler |

The soluble granules are obtained by mixing the above components according to the recipe, and grinding the mixture in a pine-disc mill to form a powder, and then granulating the powder in a fluidized bed by spraying on water as granulation liquid.

Example 6

Thifensulfuron methyl 18 g/L+Fluoroxypyr 180 g/L ZC

| EXAMPLE 6: Thifensulfuron methyl 18 g/L + Fluroxypyr 180 g/L ZC (with safener) | | COMPARISON F: Thifensulfuron methyl 18 g/L + Fluroxypyr 180 g/L ZC(without safener) | | |
|---|---|---|---|---|
| Component | Composition | Component | Composition | Remark |
| Thifensulfuron (technical) | 18 g | Thifensulfuron (technical) | 18 g | Active ingredient |
| Fluroxypyr (technical) | 180 g | Fluroxypyr (technical) | 180 g | Active ingredient |
| O,O-dipropyl-O-phenyl phosphorothioate | 90 g | O,O-dipropyl-O-phenyl phosphorothioate | 0 | safener |
| Atlox 4913 | 40 g | Atlox 4913 | 40 g | Dispersing agent |
| Citric acid | 0.5 g | Citric acid | 0.5 g | acid |
| Triethyl amine 20% emulsion | 1 g | Triethyl amine 20% emulsion | 1 g | catalysit |
| PAPI | 13.5 g | PAPI | 13.5 g | Wall-forming agent |
| water | Balance to 1 L | water | Balance to 1 L | diluent |

Fluoroxypyr CS preparation: The PAPI and Fluoroxypyr were combined with stirring to form a uniform liquid mixture. A solution of Atlox 4913 in water was heated in a Waring blender cup to about 50° C. The solution was agitated while the liquid mixture was slowly added, to form a uniform emulsion of the water immiscible phase dispersed evenly throughout the continuous aqueous phase. The aqueous solution of triethyl amine was added slowly, upon which interfacial polymerization occurred, producing microcapsules having a particle size of from 1 to 30 microns. The resulting product was cooled and filtered, to obtain a stable CS formulation of microencapsulated fluoroxypyr.

Thifensulfuron SC preparation: Atlox 4913, thifensulfuron-methyl, safener and water were combined with mixing and finely milled to form a suspension concentrate (SC).

Finally, the CS formulation of microencapsulated fluoroxypyr and the SC formulation of thifensulfuron-methyl were combined with mixing, to form a stable composition, with both microencapsulated fluoroxypyr and thifensulfuron-methyl.

Example 7

75% Thifensulfuron methyl WG

| EXAMPLE 7: 75% Thifensulfuron-methyl WG (with safener) | | COMPARISON G: 75% Thifensulfuron-methyl WG (without safener) | | |
|---|---|---|---|---|
| Component | Composition | Component | Composition | Remark |
| Thifensulfuron-methyl (technical) | 75% | Thifensulfuron-methyl (techical) | 75% | Active ingredient |
| O,O-dibutyl-O-phenyl phosphorothioate | 10% | O,O-dibutyl-O-phenyl phosphorothioate | 0 | safener |

| EXAMPLE 7: 75% Thifensulfuron-methyl WG (with safener) | | COMPARISON G: 75% Thifensulfuron-methyl WG (without safener) | | |
|---|---|---|---|---|
| Component | Composition | Component | Composition | Remark |
| Sodium dodecylphenylsulfonate | 5% | Sodium dodecylphenylsulfonate | 5% | Dispersing agent |
| Naphthalene sulphonate, sodium salt | 2.6% | Naphthalene sulphonate, sodium salt | 2.6% | Wetting agent |
| Mannitol | Balance to 100% | Mannitol | Balance to 100% | filler |

The water-dispersible granules are obtained by mixing the above components according to the recipe, and grinding the mixture in a pine-disc mill to form a powder, and then granulating the powder in a fluidized bed by spraying on water as granulation liquid.

Example 8

68.2% Thifensulfuron-methyl+6.8% Metsulfuron methyl WG

| EXAMPLE 8: 68.2% Thifensulfuron-methyl + 6.8% Metsulfuron methyl WG (with safener) | | COMPARISON H: 68.2% Thifensulfuron-methyl + 6.8% Metsulfuron methyl WG (without safener) | | |
|---|---|---|---|---|
| Component | Composition | Component | Composition | Remark |
| Thifensulfuron-methyl (technical) | 68.2% | Thifensulfuron-methyl (technical) | 68.2% | Active ingredient |
| Metsulfuron-methyl (technical) | 6.8% | Metsulfuron-methyl (technical) | 6.8% | Active ingredient |
| O,O-dibutyl-O-phenyl phosphorothioate | 15% | O,O-dibutyl-O-phenyl phosphorothioate | 0 | safener |
| Sodium dodecylphenylsulfonate | 3% | Sodium dodecylphenylsulfonate | 3% | Dispersing agent |
| Naphthalene sulphonate, sodium salt | 1.6% | Naphthalene sulphonate, sodium salt | 1.6% | Wetting agent |
| Mannitol | Balance to 100% | Mannitol | Balance to 100% | filler |

The water-dispersible granules are obtained by mixing the above components according to the recipe, and grinding the mixture in a pine-disc mill to form a powder, and then granulating the powder in a fluidized bed by spraying on water as granulation liquid.

Each of the examples described above provides two compositions, one with a combination of sulfonylurea and/or sulfonamide herbicide and a safener as disclosed herein, and the other containing the same components in the same relative amounts, but wherein the safener has been replaced by inert filler. The compositions are therefore suitable for a side-by-side comparison illustrating the unexpected advantages of the combination of a sulfonylurea and/or sulfonamide herbicide and a safener as described herein.

Biological Examples

Seeds of maize, barley, rice and corn are placed in sandy loam soil in plastic pots, and the plants are grown in the greenhouse until they have reached the 4- to 6-leaf stage and then treated post-emergence in succession with the compounds according to the invention and the herbicides. The compositions of Example 1 to Example 8 and of Comparison A to Comparison H are applied in the form of aqueous suspensions at an application rate of 300 L of water/ha (converted). 4 weeks after the treatment, the plants are scored for phytotoxicity of the applied composition, and the extent of the damage is determined by comparison with the results of treatment with Comparison A to Comparison H.

The test results, show in table 1, 2, 3 and 4 demonstrate that the compounds with safeners as described herein can prevent damage to plants in highly efficient manner.

TABLE 1

Effect of the compositions described herein on cotton plants

| | Dosage rate | Herbicidal activity in cotton(in %) | |
|---|---|---|---|
| Examples | (kg a.i./ha) | 4-leaf stage | 6-leaf stage |
| Example 1 | 0.2 | 5 | 0 |
| Comparison A | 0.2 | 75 | 60 |
| Exmaple2 | 0.2 | 0 | 0 |
| Comparison B | 0.2 | 80 | 77 |
| Example 3 | 0.2 | 0 | 0 |
| Comparison C | 0.2 | 78 | 86 |
| Example 4 | 0.2 | 0 | 0 |
| Comparison D | 0.2 | 40 | 30 |
| Example 5 | 0.2 | 0 | 0 |
| Comparison E | 0.2 | 40 | 30 |
| Example 6 | 0.2 | 0 | 0 |
| Comparison F | 0.2 | 30 | 25 |

TABLE 1-continued

Effect of the compositions described herein on cotton plants

| Examples | Dosage rate (kg a.i./ha) | Herbicidal activity in cotton(in %) | |
|---|---|---|---|
| | | 4-leaf stage | 6-leaf stage |
| Example 7 | 0.2 | 10 | 5 |
| Comparison G | 0.2 | 83 | 80 |
| Example 8 | 0.2 | 5 | 0 |
| Comparison H | 0.2 | 85 | 82 |

As can be readily seen from the results above, the use of a safener with sulfonylurea and/or sulfonamide herbicides tested provided a reduction in injury of 100% (Example 1/Comparison A (6-leaf stage), Example 2/Comparison B (both stages), Example 3/Comparison C (both stages), Example 4/Comparison D (both stages), Example 5/Comparison E (both stages), Example 6/Comparison F (both stages), and Example 8/Comparison H (6-leaf stage), 93% (Example 1/Comparison A (4-leaf stage)), 87.9% (Example 7/Comparison G (4-leaf stage)), 93.8% (Example 7/Comparison G (6-leaf stage)), and 94.1% (Example 8/Comparison H (4-leaf stage)). Each of these reductions is surprisingly well above those mentioned for safening of clomazone by dietholate in U.S. Pat. No. 6,855,667.

TABLE 2

Effect of the compositions described herein on corn plants

| Examples | Dosage rate (kg a.i./ha) | Herbicidal activity in corn (in %) | |
|---|---|---|---|
| | | 4-leaf stage | 6-leaf stage |
| Example 1 | 0.3 | 5 | 0 |
| Comparison A | 0.3 | 80 | 75 |
| Example 2 | 0.3 | 0 | 0 |
| Comparison B | 0.3 | 85 | 88 |
| Example 3 | 0.3 | 10 | 5 |
| Comparison C | 0.3 | 90 | 85 |
| Example 4 | 0.3 | 0 | 0 |
| Comparison D | 0.3 | 40 | 30 |
| Example 5 | 0.3 | 0 | 0 |
| Comparison E | 0.3 | 10 | 15 |
| Example 6 | 0.3 | 0 | 0 |
| Comparison F | 0.3 | 15 | 13 |
| Example 7 | 0.3 | 15 | 5 |
| Comparison G | 0.3 | 90 | 88 |
| Example 8 | 0.3 | 10 | 5 |
| Comparison H | 0.3 | 92 | 88 |

As can be readily seen from the results above, the use of a safener with sulfonylurea and/or sulfonamide herbicides tested provided a reduction in injury of 100% (Example 1/Comparison A (6-leaf stage), Example 2/Comparison B (both stages), Example 4/Comparison D (both stages), Example 5/Comparison E (both stages), Example 6/Comparison F (both stages)), 93.4% (Example 1/Comparison A (4-leaf stage)), 88.9% and 94.1% (Example 3/Comparison C (4-leaf stage and 6-leaf stage, respectively)), 83.3% and 94.3% (Example 7/Comparison G (4-leaf stage and 6-leaf stage, respectively)), and 89.1% and 94.3% (Example 8/Comparison H (4-leaf stage and 6-leaf stage, respectively). As with the results for cotton, the results for corn show reductions that are surprisingly well above those mentioned for safening of clomazone by dietholate in U.S. Pat. No. 6,855,667.

TABLE 3

Effect of the compositions described herein on rice plants

| Examples | Dosage rate (kg a.i./ha) | Herbicidal activity in rice (in %) | |
|---|---|---|---|
| | | 4-leaf stage | 6-leaf stage |
| Example 1 | 0.075 | 5 | 0 |
| Comparison A | 0.075 | 70 | 65 |
| Example 2 | 0.075 | 0 | 0 |
| Comparison B | 0.075 | 75 | 78 |
| Example 3 | 0.075 | 10 | 5 |
| Comparison C | 0.075 | 70 | 75 |
| Example 4 | 0.075 | 0 | 0 |
| Comparison D | 0.075 | 40 | 20 |
| Example 5 | 0.075 | 0 | 0 |
| Comparison E | 0.075 | 10 | 15 |
| Example 6 | 0.075 | 0 | 0 |
| Comparison F | 0.075 | 15 | 13 |
| Example 7 | 0.075 | 10 | 0 |
| Comparison G | 0.075 | 80 | 78 |
| Example 8 | 0.075 | 5 | 0 |
| Comparison H | 0.075 | 82 | 78 |

As can be readily seen from the results above, the use of a safener with sulfonylurea and/or sulfonamide herbicides tested provided a reduction in injury of 100% (Example 1/Comparison A (6-leaf stage), Example 2/Comparison B (both stages), Example 4/Comparison D (both stages), Example 5/Comparison E (both stages), Example 6/Comparison F (both stages), Example 7/Comparison G (6-leaf stage), Example 8/Comparison H (6-leaf stage)), 92.8% (Example 1/Comparison A (4-leaf stage)), 85.7% and 93.3% (Example 3/Comparison 3 (4-leaf stage and 6-leaf stage, respectively)), 75% (Example 7/Comparison G (4-leaf stage)), and 93.9% (Example 8/Comparison H (4-leaf stage)). Of these reductions, only Example 7/Comparison G (4-leaf stage) is even close to the reductions obtained for dietholate with clomazone as reported in U.S. Pat. No. 6,855,667; all of the remaining reductions in injury are surprisingly well above the results obtained for clomazone.

TABLE 4

Effect of the compositions described herein on barley plants

| Examples | Dosage rate (kg a.i./ha) | Herbicidal activity in barley (in %) | |
|---|---|---|---|
| | | 4-leaf stage | 6-leaf stage |
| Example 1 | 0.2 | 5 | 0 |
| Comparison A | 0.2 | 69 | 67 |
| Example 2 | 0.2 | 0 | 0 |
| Comparison B | 0.2 | 73 | 75 |
| Example 3 | 0.2 | 7 | 4 |
| Comparison C | 0.2 | 74 | 70 |
| Example 4 | 0.2 | 0 | 0 |
| Comparison D | 0.2 | 36 | 23 |
| Example 5 | 0.2 | 0 | 0 |
| Comparison E | 0.2 | 12 | 13 |
| Example 6 | 0.2 | 0 | 0 |
| Comparison F | 0.2 | 17 | 13 |
| Example 7 | 0.2 | 10 | 0 |
| Comparison G | 0.2 | 80 | 74 |
| Example 8 | 0.2 | 5 | 0 |
| Comparison H | 0.2 | 85 | 74 |

As can be readily seen from the results above, the use of a safener with sulfonylurea and/or sulfonamide herbicides tested provided a reduction in injury of 100% (Example 1/Comparison A (6-leaf stage), Example 2/Comparison B (both stages), Example 4/Comparison D (both stages), Example 5/Comparison E (both stages), Example 6/Comparison F (both stages), Example 7/Comparison G (6-leaf stage), Example 8/Comparison H (6-leaf stage)), 92.3% (Example 1/Comparison A (4-leaf stage)), 90.5% and 94.3% (Example 3/Comparison C (4-leaf stage and 6-leaf stage, respectively)), 87.5 (Example 7/Comparison G (4-leaf stage)), and 94.1 (Example 8/Comparison H (4-leaf stage)). Each of these reductions is surprisingly well above those mentioned for safening of clomazone by diethotate in U.S. Pat. No. 6,855,667.

The results show that, for a variety of crop plants, and for a variety of sulfonylurea and sulfonamide herbicides, the safeners described herein provide a degree of injury reduction that is unexpected in light of the low injury reduction provided by using diethotate with clomazone as reported in U.S. Pat. No. 6,855,667.

The invention having been described with respect to certain specific embodiments and examples thereof, it will be understood that these embodiments and examples are not limiting of the scope of the appended claims.

The invention claimed is:

1. A herbicidal composition, comprising
A) an antidotically effective amount of one or more safeners from the group of the phosphorated esters of the formula (I) (component A):

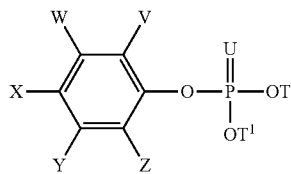

wherein T, T¹ are independently selected from the group of hydrogen, alkyl, haloalkyl, alkoxyalkyl, alkenyl, and alkynyl; U is O or S, and V, W, X, Y, and Z are independently selected from the group of hydrogen, halogen, alkyl, haloalkyl, and alkoxy; and
B) a herbicidally effective amount of one or more herbicides (component B) selected from the group consisting of rimsulfuron, metsulfuron-methyl, nicossulfuron, and tribenuron-methyl.

2. The composition according to claim 1, wherein components A and B are present in a weight ratio of component A to component B ranging from approximately 1:10 to approximately 10:1.

3. The composition according to claim 2, wherein the weight ratio of component A to component B ranges from approximately 1:10 to approximately 5:1.

4. The composition according to claim 1, wherein T and T¹ are independently selected from alkyl of 1-7 carbon atoms.

5. The composition according to claim 4, wherein T and T¹ are independently selected from methyl, ethyl, propyl, and butyl.

6. The composition according to claim 5, wherein T and T¹ are the same.

7. The composition according to claim 1, wherein T and T¹ are methyl, U is sulfur, and V, W, X, Y and Z are hydrogen.

8. The composition according to claim 1, wherein T and T¹ are ethyl, U is sulfur, and V, W, X, Y and Z are hydrogen.

9. The composition according to claim 1, wherein T and T¹ are propyl, U is sulfur, and V, W, X, Y and Z are hydrogen.

10. The composition according to claim 1, wherein T and T¹ are butyl, U is sulfur, and V, W, X, Y and Z are hydrogen.

11. A method of protecting a plant from phytotoxic injury from application of a herbicidally effective amount of a herbicidal compound to the locus of said plant, which method comprises: applying to said locus an effective amount of one or more safening compounds having formula (I) (component A)

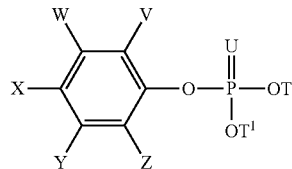

wherein T, T¹ are independently selected from the group of hydrogen, alkyl, haloalkyl, alkoxyalkyl, alkenyl, and alkylnyl; U is O or S, and, W, X, Y, and Z are independently selected from the group of hydrogen, halogen, alkyl, haloalkyl, and alkoxy; and
applying to said locus a herbicidally effective amount of one or more herbicides (component B) selected from the group consisting of rimsulfuron, metsulfuron-methyl, nicosulfuron, and tribenuron-methyl.

12. The method according to claim 11, wherein said applying of components A and B occurs simultaneously and in a weight ratio of component A to component B ranging from about 1:10 to about 10:1.

13. The method according to claim 12, wherein said weight ratio of component A to component B ranges from about 1:10 to about 5:1.

14. The method according to claim 11, wherein T and T¹ are independently selected from alkyl of 1-7 carbon atoms.

15. The composition according to claim 14, wherein T and T¹ are independently selected from methyl, ethyl, propyl, and butyl.

16. The composition according to claim 15, wherein T and T¹ are the same.

17. The method according to claim 11, wherein T and T¹ are methyl, U is sulfur, and V, W, X, Y and Z are hydrogen.

18. The method according to claim 11, wherein T and T¹ are ethyl, U is sulfur, and V, W, X, Y and Z are hydrogen.

19. The method according to claim 11, wherein T and T¹ are propyl, U is sulfur, and V, W, X, Y and Z are hydrogen.

20. The method according to claim 11, wherein T and T¹ are butyl, U is sulfur, and V, W, X, Y and Z are hydrogen.

21. The method according to claim 11, wherein said plant is selected from the group of soybean, cotton, sugarbeet, rape, potato, sunflower, peanut, lettuce, carrot, sweet potato, alfalfa, tobacco, corn, rice, sorghum, wheat, barley, oats, rye, triticale, and sugarcane.

22. The method according to claim 21, wherein said plant is barley, rice, corn or cotton.

23. The method according to claim 11, wherein said herbicidal compound (component B) is applied to the locus of said plant in an amount of about 0.001 to about 15 kilograms/hectare and said safening compound (component A) is applied in a amount of about 0.003 to about 15 kilograms/hectare.

24. The method according to claim 11, wherein said component A further comprises an agriculturally acceptable carrier.

* * * * *